United States Patent [19]

Chase et al.

[11] 4,218,569

[45] Aug. 19, 1980

[54] METHOD FOR PROCESSING ETHERIFIED LIGHT HYDROCARBON MIXTURES TO REMOVE METHANOL

[75] Inventors: John D. Chase, Oakville; Buenaventura B. Galvez, Islington; Bruce W. Kennedy, Toronto, all of Canada

[73] Assignee: Gulf Canada Limited, Toronto, Canada

[21] Appl. No.: 886,366

[22] Filed: Mar. 14, 1978

[51] Int. Cl.² .................... C07C 41/06; C07C 41/12
[52] U.S. Cl. .................... 568/697; 568/699; 585/518; 585/519; 585/717; 585/800; 585/832
[58] Field of Search ......... 260/614 A, 683.43, 683.49; 568/918, 697, 699; 585/518, 519, 717, 800, 832

[56] References Cited

U.S. PATENT DOCUMENTS

| | | | |
|---|---|---|---|
| 2,542,454 | 2/1951 | Arnold | 260/450 |
| 2,580,750 | 1/1952 | Fleming | 260/450 |
| 2,671,104 | 3/1954 | Grahame et al. | 260/450 |
| 3,388,046 | 6/1968 | Hendrix | 568/918 X |
| 3,726,942 | 4/1973 | Louder | 260/614 A UX |
| 3,846,088 | 11/1974 | Brown et al. | 260/614 A |

FOREIGN PATENT DOCUMENTS

| | | | |
|---|---|---|---|
| 1173128 | 12/1969 | United Kingdom | 260/614 A |
| 1369889 | 10/1974 | United Kingdom | 260/614 A |
| 498956 | 1/1976 | U.S.S.R. | |

OTHER PUBLICATIONS

Perry, Chemical Engineers Handbook, McGraw-Hill Book Co., New York, 4th ed., 1963, 14-40, 14-41, 14-42, 18-3.

*Primary Examiner*—Howard T. Mars
*Attorney, Agent, or Firm*—D. R. Morrison

[57] ABSTRACT

Mixed hydrocarbons of predominantly four carbon atoms each are subjected to etherification with methanol, to make ether from the tertiary olefin in the mixture; the unreacted hydrocarbons, after separation from the ether by distillation, are contaminated with methanol which is removed by absorption or extraction with a glycol before the hydrocarbons are subjected to further processing in which the methanol is detrimental.

8 Claims, No Drawings

METHOD FOR PROCESSING ETHERIFIED LIGHT HYDROCARBON MIXTURES TO REMOVE METHANOL

This invention relates to improvements in refining of petroleum refinery streams, more particularly light olefinic hydrocarbon streams containing predominantly hydrocarbons of four carbon atoms each, and specifically to a method in which such streams are subject to etherification with methanol for the production of dialkyl ethers from their tertiary olefin content.

It has been suggested in the prior art, particularly in copending application Ser. No. 863,499 filed Dec. 22, 1977 that tertiary branched chain olefins in light catalytically cracked gasoline (LCCG) and in partially hydrogenated pyrolysis gasoline (HPGB or dripolene) are advantageously converted to dialkyl ethers by etherifying them with primary alcohol, either in admixture with one another or separately subsequent to substantial separation by fractionation of the tertiary olefins of differing number of carbon atoms into separate hydrocarbon fractions. It has also been suggested in the art that, subsequent, to etherification of tertiary olefins in such gasolines or hydrocarbon fractions, other hydrocarbons in the fractions can be processed, for example by alkylation, to increase octane value of the material and/or reduce its volatility as a gasoline component. In U.S. Pat. No. 3,482,952 it is acknowledged that alkylation of the material, while it still contains unreacted alcohol from the etherification, results in high consumption of acidic alkylation catalyst, and fractional distillation of the etherified material is recommended to separate a low boiling olefin rich fraction from a less volatile ether rich fraction; thereafter the more volatile olefin rich fraction, having reduced alcohol content, is alkylated.

It has now been found that, particularly when a mixed hydrocarbon fraction containing predominantly hydrocarbons of only four carbon atoms is processed in this manner, it is not possible to achieve the necessary separation of methanol from the low boiling, olefin rich fraction by simple fractional distillation. Petroleum refineries having an alkylation unit using hydrofluoric acid catalyst, or a polymerization (polygas) unit using phosphoric acid catalyst, prefer a feed stream for such unit to contain less than substantially 100 mole ppm of methanol. It has been discovered that a minimum boiling azeotrope of methanol and n-butane exists, although its existence does not appear to have been reported in the chemical literature. This azeotrope prevents the efficient separation of methanol, by simple fractional distillation, from hydrocarbon fractions containing n-butane which generally is present in significant amounts in such fractions following etherification of the tertiary olefins therein. Hence the recommendation in U.S. Pat. No. 3,482,952 for etherification with methanol of the tertiary olefins in $C_4$-$C_6$ mixed hydrocarbon fractions, followed by distillation separation of a more volatile, unetherified hydrocarbon portion and alkylation of the separated unetherified portion, is not practicable, particularly when the original mixed hydrocarbon fraction to be etherified contains predominantly hydrocarbons of only four carbon atoms. The present invention was developed particularly to provide a method of processing an olefinic mixed hydrocarbon stream containing predominantly hydrocarbons of only four carbon atoms whereby the tertiary olefin therein is substantially etherified with methanol and a portion of the unetherified hydrocarbons, separated as a distillate from the ether containing residue, is refined to a quality satisfactory for further utilization in gasoline alkylate and polygas production. Such olefinic mixed hydrocarbon streams to be etherified are available, for example, from the effluent of a fluid catalytic cracking unit, from the effluent of a thermal or steam cracker used primarily for ethylene production, and various other sources of mixed olefinic hydrocarbons of predominantly four carbon atoms.

The invention thus consists in a method for processing an olefinic mixed hydrocarbon stream containing predominantly hydrocarbons of only four carbon atoms each including n-butane and isobutylene, said method comprising:

1. passing the stream in admixture with methanol into contact with an etherification catalyst, in a reactor under etherifying conditions, to etherify tertiary olefins in the stream, 2. passing the resulting ether and mixed hydrocarbon containing effluent to a fractional distillation column and distilling to provide (a) a substantially ether-free distillate containing a proportion of methanol distilling azeotropically with n-butane in the distillate and (b) a distillation residue containing substantially all of the ether from the effluent, 3. passing said distillate through a methanol removal unit in contact with a stream of methanol miscible liquid which is ethylene glycol, diethylene glycol, triethylene glycol, propylene glycol, or a mixture of any of these, to remove methanol from the distillate, and 4. separating distillate of reduced methanol content from said liquid.

The catalytic etherification of tertiary olefins, particularly isobutylene with methanol, is a well-known art and modern catalytic processes therefor can readily achieve single pass conversions to ether of up to 82% or more of the isobutylene content of olefinic mixed hydrocarbon streams containing predominantly four carbon atoms. Sometimes a slight excess of methanol to stoichiometric reaction with the isobutylene is used in the etherification reactor, in order to improve isobutylene conversion, but even without such an excess, there is bound to be some methanol in the etherification reactor effluent as the reaction cannot proceed past the point of equilibrium concentration of the methanol and ether product. When the effluent is distilled, the residual methanol can be largely retained in the distillation residue with the higher boiling ether product, for blending into gasoline for example, but some of it must distill overhead from the effluent as the azeotrope with n-butane previously mentioned herein; unreacted butenes also readily distill overhead from the effluent. The foregoing overhead distillate contains a high proportion of butenes which can advantageously be reacted by alkylation to form alkylate or by polymerization to form polygas for blending into gasoline, but the methanol in the distillate must first be reduced to a much lower concentration to preclude interference with the catalysts used in either of the foregoing reactions. Both alkylation and polymerization reactions use strongly acidic catalyst which also, for example, promote etherification of methanol to dimethyl ether under the reaction conditions, forming water as a co-product, and this water is detrimental to the strongly acidic catalysts. Also, the dimethyl ether is a low boiling ether, undesirable as a gasoline component. Furthermore, methanol may react with strong acids, thus destroying them and precluding them exercising any further desired catalytic activity.

Because the binary azeotrope of methanol and n-butane is a minimum boiling azeotrope generally containing in the range from only one to six percent methanol by weight, it is not practicable from an economic viewpoint to separate methanol from the predominantly $C_4$ hydrocarbon distillate by further distillation prior to using the latter as feed in an alkylation or polygas unit. The foregoing azeotropic proportions of methanol and n-butane relate to the most relevant pressure range from one to four atmospheres. With higher pressure the azeotropic composition of methanol and n-butane has higher proportions of methanol. Available measurements showing the effect of pressure on the azeotropic composition are given in the following Table 1.

TABLE 1

| Effect of Pressure on Composition of Normal Butane-Methanol Azeotrope | | | | |
|---|---|---|---|---|
| Pressure (Atm. Ab.) | 1.70 | 2.72 | 4.08 | 5.44 |
| Wt. % Methanol | 1.0 | 2.4 | 4.3 | 6.1 |
| Wt. % n-butane | 99.0 | 97.6 | 95.7 | 93.9 |

The reduction of methanol concentration which must be achieved in any particular application of the invention depends on the particular type of downstream process that utilizes the hydrocarbon stream. The exact value of the maximum permissible level of methanol in the feed to such downstream process can be assessed for example by balancing the capital and operating cost of methanol removal equipment against the detrimental effect a specified methanol concentration has on the downstream process. Current experience using a polymerization reactor downstream indicates that methanol concentration should be reduced to no greater than 100 mole ppm by the methanol removal unit in the method of this invention before the mixed hydrocarbon distillate is fed to the polymerization reactor. Similarly it is felt that methanol concentrations should be reduced to no greater than 300 mole ppm methanol and 50 mole ppm methanol respectively before the mixed hydrocarbon distillate is fed to alkylation process reactors utilizing sulfuric acid and hydrofluoric acid catalysts respectively.

Methanol removal units suitable for use in the present invention can be of either the liquid-liquid extractor type or the gas absorber type. A gas absorber type is used when it is desired to operate at temperature and pressure under which the distillate containing methanol and predominantly $C_4$ hydrocarbons is in the vapor phase; ethylene glycol is the most practicable scrubbing liquid to use as the absorbant, because it is an efficient absorber of the methanol while it minimizes absorption of hydrocarbons of the distillate, and it is readily subsequently separated from the methanol by simple distillation from which both the methanol and ethylene glycol can be recovered for reuse. Liquid-liquid extractors for removing methanol from the predominantly $C_4$ hydrocarbon distillate can use any of several methanol miscible glycols as the extracting liquid. Ethylene glycol is preferred, for the reason noted above that it is readily separated from the extracted methanol by simple distillation, for recovery and reuse of both materials. Diethylene glycol, triethylene glycol (which are ethers of ethylene glycol), and propylene glycol are other suitable glycols.

When using a gas absorber type of methanol removal unit to remove methanol from a vapor phase stream of effluent in accordance with the present invention, the unit may operate at temperatures in the range from substantially 34° F. (1° C.) to substantially 450° F. (232° C.). Preferably temperature in the range from 70° F. to 200° F. (21° C. to 93° C.) is used. The mole flow rate of glycol absorption liquid in the absorber, in proportion to the mole flow rate of hydrocarbon vapors containing methanol, may be in the range from substantially 0.08 to substantially 5.0; preferably it is in the range from 0.15 to 0.5.

When using liquid-liquid extraction with glycol in the methanol removal unit in the process of this invention, the unit may operate at temperatures in the range from substantially 8° F. (−13° C.) to substantially 350° F. (177° C.); preferably the temperature is in the range from 50° F. to 150° F. (10° C. to 65° C.). Obviously pressure in the liquid-liquid extraction unit must be higher than in a gas absorber unit operating at the same temperature, in order to maintain the hydrocarbons in the liquid phase. The mole flow rate of glycol through a liquid-liquid extraction, in proportion to the mole flow rate of liquid hydrocarbons containing methanol, may be in the range from substantially 0.15 to substantially 6.0; preferably it is in the range from 0.24 to 0.6.

The equipment for the methanol removal unit of either the liquid-liquid extraction type or the gas absorption type in the method of this invention can be any of the suitable conventional types available for such operations. For example, both packed and plate type vapor-liquid contacting columns can be used, plate type columns normally being more efficient per unit height than packed columns for absorption but the latter having lower capital cost. Similar considerations apply to counter-current liquid-liquid extraction columns, but for extraction, packed columns are generally preferred. Either counter-current or co-current flows can be used, but counter-current is generally more efficient. Alternatively a series of mixers and settlers may be used for contacting and separating various stages during liquid-liquid extraction.

The methanol miscible liquid used in the methanol removal unit preferably is monoethylene glycol because of its effectiveness and relatively low cost. The higher molecular weight glycols: diethylene glycol, triethylene glycol, and propylene glycol, are generally more expensive without being significantly more effective.

In the initial step of the method of this invention, which step is generally a conventional catalytic etherification with methanol of the isoolefin components of a fraction of mixed hydrocarbons of predominantly four carbon atoms, the mole ratio of methanol to isoolefin in the feed is generally in the range from 0.7:1 to 1.3:1 and preferably is in the range from 0.9:1.0, most preferably 0.95:1. Preferred catalysts for the conventional etherifications are the polystyrene-divinyl benzene type cation exchange resins. Temperatures for the etherification are generally in the range from 150° F. to 250° F. (65° C. to 121° C.) and pressures are at least sufficiently high to maintain the etherification reaction mixtures in the liquid phase. An example of conditions for a typical etherification of a $C_4$ hydrocarbon fraction containing 19% isobutylene includes a temperature of 180° F., a pressure of 18 atmospheres, and a methanol: isoolefin feed ratio of 0.95; under such conditions a conversion of 82% of the isobutylene is obtained using conventional ion exchange resin catalyst.

In the second step of the method of this invention, the effluent from the preceding etherification step is fractionally distilled. The effluent from the preceding step typically contains, for example, 23% ether (primarily MTBE, i.e. methyl tertiarybutyl ether), 76% hydrocarbons (primarily C₄ hydrocarbons) and 1% methanol. The distillation is conducted under conditions of temperature, pressure and reflux such that substantially all of the ether fed to the column is withdrawn in the higher boiling bottom fraction and none of it passes overhead in the distillate fraction, while at the same time most of the hydrocarbons are withdrawn in the distillate. Under these conditions, most of the methanol in the effluent remains in the higher boiling bottom fraction but, because of the formation of the binary azeotrope of methanol and n-butane, some of the methanol appears in the primarily hydrocarbon distillate. In achieving the separation of the hydrocarbon distillate from the ether containing bottom fraction, a proportion of, for example, 84% of the butane in the hydrocarbon fraction distills into the distillate, the balance remaining with the ether fraction. Typically this 84% portion of the butane constitutes a proportion of, for example, 8% by weight of the hydrocarbon distillate and brings with it into the distillate an azeotrope with methanol, the proportion of methanol in the distillate partially depending on the pressure maintained during distillation and also on the proportion of n-butane in the distillate. Typically there is, for example, a proportion of 0.4% by weight of methanol in the distillate containing 6% n-butane, from a column operating at 3.7 atmospheres pressure.

This invention may be more readily understood from the following examples of specific embodiments thereof which are given for illustration only and not to limit the ensuing claims. The proportions give therein and throughout the rest of the specification and claims are proportions by weight unless otherwise specifically indicated.

EXAMPLE 1

An olefinic mixed hydrocarbon fraction containing predominantly hydrocarbons of four carbon atoms including 19% by weight isobutylene and derived from the effluent of a fluid catalytic cracking process was mixed with methanol in a proportion of substantially 0.95 mole of methanol per mole of isobutylene in the fraction and passed in liquid phase into contact with an etherification catalyst of ion exchange resin under etherifying temperature conditions at a liquid hourly space velocity of substantially 3.0. Reactor effluent containing 76% by weight of C₄ hydrocarbons, 23% by weight of methyl tertiarybutyl ether, and 1% by weight of methanol was fractionally distilled in a 40 plate distillation column operating at a pressure of 3.7 atmospheres to separate a bottom fraction, containing substantially all of the ether together with most of the methanol fed to the column and some of the hydrocarbons, from a distillate substantially free of ether and containing 0.7 mole percent (0.4% by weight) methanol, balance hydrocarbons including 8% by weight n-butane. The distillate was fed at a rate of 3.3 lbs. per hour (1.5 kg/hr) to the bottom of a sieve tray gas absorber column one inch (2.5 cm) in diameter, having 7 trays and being maintained at atmospheric pressure; a counter-current stream of ethylene glycol maintained at 72° F. (22° C.) was fed to the top of the column at a mole rate of 0.25 compared to the feed of distillate. The glycol flowing down through the column contacted the distillate which, under the temperature and pressure conditions in the column, was in the vapor phase. The vapor phase effluent withdrawn from the top of the column contained 30 mole ppm methanol in a hydrocarbon mixture which was eminently suitable as feed to a hydrofluoric acid catalyzed alkylation process; thus 99.5% of the methanol fed to the absorber column was removed by the ethylene glycol which was withdrawn from the bottom of the column and fed to a packed stripping column. In the stripping column methanol was stripped from the glycol for recycle to the etherification unit and glycol, withdrawn from the bottom of the stripping column and containing a residual 240 mole ppm methanol, was recycled to the top of the absorber column.

EXAMPLE 2

This example illustrates the use of liquid-liquid extraction of methanol from a hydrocarbon stream using ethylene glycol as the extractant. The hydrocarbon distillate stream of 3.2 lbs/hr (1.45 kg) C₄ hydrocarbons containing 0.7 mole percent methanol, fed in the preceding example to a gas absorber column, was directed instead into the bottom of an extraction column five feet (1.52 m) high, two inches (5 cm) in diameter, packed with half inch (1.25 cm) Raschig rings, and maintained at a pressure of 3.5 atmospheres. A counter-current stream of ethylene glycol maintained at 78° F. (26° C.) was fed to the top of the column at a mole rate relative to the distillate fed of 0.36. At the temperature and pressure condition in the extractor, the distillate remained in the liquid phase. The liquid hydrocarbon stream withdrawn from the top of the extractor contained 95 mole ppm methanol, and was suitable as feed to a polygas unit. Ethylene glycol withdrawn from the bottom of the extractor was fed to a stripping column to strip methanol therefrom and the stripped glycol containing 180 mole ppm methanol was recycled to the top of the extractor.

Numerous modifications of the specific expedients described herein can be made without departing from the scope of the invention which is defined in the following claims.

What is claimed is:

1. A method for processing an olefinic mixed hydrocarbon stream containing predominantly hydrocarbons of only four carbon atoms each including n-butane and isobutylene, said method comprising:
   (i) passing the stream in admixture with methanol in contact with an etherification catalyst, in a reactor under etherifying conditions, to etherify tertiary olefins in the stream,
   (ii) passing the resulting ether and mixed hydrocarbon containing effluent to a fractional distillation column and distilling to provide (a) a substantially ether-free distillate containing a proportion of methanol distilling azeotropically with n-butane in the distillate and (b) a distillation residue containing substantially all of the ether from the effluent,
   (iii) passing said distillate through a methanol removal unit in contact with a stream of methanol miscible liquid which is ethylene glycol, diethylene glycol, triethylene glycol, propylene glycol, or a mixture of any of these to remove methanol from the distillate, and
   (iv) separating distillate of reduced methanol content from said liquid.

2. A method as claimed in claim 1 in which the methanol removal unit is a gas absorber, the methanol miscible liquid is ethylene glycol, the distillate is passed into said absorber in the vapor phase, and methanol vapor is absorbed therefrom into the liquid phase ethylene glycol.

3. A method as claimed in claim 2 in which the gas absorber is maintained at temperature in the range from 34° F. to 450° F. (1° C. to 232° C.) and the ratio of the mole flow rate of ethylene glycol to the mole flow rate of distillate vapor therein is in the range from 0.08 to 5.0.

4. A method as claimed in claim 3 in which the temperature is in the range from 70° F. to 200° F. (21° C. to 93° C.) and the ratio of the mole flow rates is in the range from 0.15 to 0.5.

5. A method as claimed in claim 1 in which the methanol removal unit is a liquid-liquid extractor, the distillate is passed thereto in liquid pahse, the methanol miscible liquid is ethylene glycol which extracts methanol therefrom in counter-current flow thereto through the extractor.

6. A method as claimed in claim 5 in which the liquid-liquid extractor is maintained at a temperature in the range from 8° F. to 350° F. (−13° C. to 177° C.) and the ratio of the mole flow rate of ethylene glycol to the mole flow rate of liquid distillate is in the range from 0.15 to 6.0.

7. A method as claimed in claim 6 in which the temperature is in the range from 50° F. to 150° F. (10° C. to 65° C.) and the ratio of the mole flow rates is in the range from 0.24 to 0.6.

8. In a method for processing an olefinic mixed hydrocarbon stream containing predominantly hydrocarbons of only four carbon atoms each including n-butane and isobutylene, in which said stream is admixed with methanol and contacted with an etherification catalyst under etherifying conditions to etherify tertiary olefins in the stream, the resulting admixture of hydrocarbons, ether, and unreacted methanol is fractionally distilled to separate a higher boiling fraction containing the ether product, most of the unreacted methanol, and some of the hydrocarbons from a lower boiling fraction containing predominantly hydrocarbons, and the lower boiling predominantly hydrocarbon fraction is subsequently contacted with acidic catalyst of the group of strong acid alkylation and polymerization catalysts, the improvement which comprises passing said lower boiling predominantly hydrocarbon fraction in contact with a stream of methanol miscible liquid which is ethylene glycol, diethylene glycol, triethylene glycol, propylene glycol, or a mixture of any of these, to remove methanol from the lower boiling hydrocarbon fraction, and separating the said fraction of reduced methanol content from said methanol miscible liquid, before said fraction is contacted with said strongly acidic catalyst.

* * * * *